United States Patent [19]

Dali

[11] 4,367,735

[45] Jan. 11, 1983

[54] NASAL CANNULA

[75] Inventor: Carmelo Dali, Chesire, Conn.

[73] Assignee: Novametrix Medical Systems, Inc., Wallingford, Conn.

[21] Appl. No.: 108,667

[22] Filed: Dec. 31, 1979

[51] Int. Cl.³ .................................................. A61M 25/00
[52] U.S. Cl. ............................ 128/207.18; 128/203.22; 128/207.17; 128/207.11
[58] Field of Search ..................... 128/203.18, 203.22, 128/204.12, 205.25, 206.11, 207.11, 207.18, 207.17, 204.18

[56] References Cited

U.S. PATENT DOCUMENTS

| 2,693,800 | 11/1954 | Caldwell | 128/207.18 |
| 2,751,906 | 6/1956 | Irvine | 128/206.11 |
| 3,013,556 | 12/1961 | Galleher, Jr. | 128/207.11 |
| 3,858,615 | 1/1975 | Weigl | 128/204.18 |
| 3,867,946 | 2/1975 | Huddy | 128/207.18 |
| 4,018,221 | 4/1977 | Rennie | 128/207.18 |
| 4,050,466 | 9/1977 | Koerbacher | 128/207.14 |

FOREIGN PATENT DOCUMENTS 780746  2/1935  France ........................... 128/207.11

Primary Examiner—Henry J. Recla
Attorney, Agent, or Firm—Howard F. Mandelbaum

[57] ABSTRACT

An improved nasal cannula is made of a soft pliable material and has two hollow tubular prongs which are ribbed to prevent significant closure of the airways through the prongs upon bending of the prongs and a base adapted to receive a soft strip of foam-like material which can be attached to a skull cap for securing the prongs of the cannula in the nasal passages of a patient.

9 Claims, 4 Drawing Figures

NASAL CANNULA

BACKGROUND OF THE INVENTION

This invention relates to apparatus for enabling the breathing of a patient to be assisted by means of a respirator. More specifically, the invention concerns a nasal cannula adapted to be connected between the nostrils of the patient and a hose leading to a respirator or other respiration assistance device.

Some patients having respiratory problems are assisted in breathing by a mechanical respirator which pumps ambient or oxygen enriched air directly into the lungs of the patient through a hose leading from the respirator, and an artifical airway at which the end of the hose opposite the respirator end, is terminated. Artificial airways known to the art include endotracheal tubes, tracheotomy tubes, and nasal cannulas. Unlike endotracheal tubes which are inserted into the trachea of the patient through the mouth and tracheotomy tubes which are inserted through an incision proximate the throat of the patient, nasal cannulas generally employ two hollow prongs adapted to be received in the nostrils of the nose of the patient and a tubular member in communication with the hollow prongs and the hose leading to the respirator.

Maintenance of the cannula in sealing relationship with the nostrils of the patient to prevent communication between the nostrils and ambient environment, and irritation of the nasal passages by the cannula are two problems encountered in the use of prior art nasal cannulas. These problems are aggravated upon movement of the head of the patient and are of particular concern when the patient is a neonate.

In order to overcome the problem of exposure of the nostrils to the ambient environment and resulting leakage, some prior art cannulas employ means for firmly impressing the nose against the cannula by outwardly expanding the nostrils thereby causing trauma and irritation. Some prior art nasal cannulas employ rigid prongs which are mounted on a transverse surface adapted to firmly engage the lip of the patient while the prongs are inserted into the nostrils to form an air tight seal. The use of such cannulas can result in extreme discomfort to the patient as well as the possibility of trauma and irritation within the nostrils, as previously described and to other skin surfaces of the patient.

Some prior art cannulas have addressed the problems of irritation and leakage by employing devices made of a flexible elastomeric or sponge rubber material to minimize irritation within the nostrils while forming an adequate seal thereabout. Still other prior art cannulas employ prongs having enlarged nasal end portions for forming an air tight seal with the interior engaging surfaces of the nostrils.

The use of soft and highly flexible rubber materials in nasal cannulas has an attendant disadvantage in that the prongs are likely to be compressed when bent during movement of the patient or stressed by the nostrils during breathing thereby obstructing the artificial airway through the prongs and interfering with instead of enhancing the patient's ability to breath. In prior art, cannulas which employ enlarged nasal end portions, the interface between the enlarged portions and the narrower tubular prongs generally forms a single point of weakness whereat stresses applied to the nasal cannula are likely to be concentrated thereby resulting in compression of or damage to the cannula. The problem of compression caused by movement is of particular concern when the cannula is used in a neonatal environment in which an infant's breathing is to be assisted by means of a respirator. Uncontrolled movement by the infant who cannot be alerted to the dangers of such movement is likely to result in bending of the prongs causing compression or pinching of the cannula. Interruption of or reduction in the oxygen enriched air administered to and the exhaled air withdrawn from the infant can cause serious harm to an infant whose breathing must be assisted by a respirator.

As a further means of preventing movement of the cannula within the nasal passages of the patient, numerous devices are known to the prior art for stabilizing the cannula with respect to the patient. Some devices employ the gas supply tubes which supply air from the respirator to the cannula for holding the cannula in place. For example, in U.S. Pat. No. 3,915,173 to Brekke, a cannula assembly is shown wherein portions of the gas supply tubes are seated on the bridge of the patient's nose. In U.S. Pat. No. 2,693,800, the gas supply tubes are passed over the ears of the patient. U.S. Pat. Nos. 2,168,705 and 2,245,969 also show mechanisms which are placed over the patient's ears. In U.S. Pat. No. 2,259,817, oxygen tubes are downwardly extended from a temple band encircling the head of the patient. The foregoing devices which are primarily designed for use with adults, employ substantially rigid supporting devices for the cannula device to maintain the position of the cannula with respect to the patient. The use of such rigid or semi-rigid devices to form a coupling between the cannula and a supporting skin surface on the patient is unsuitable for neonates who can be injured by such rigid devices upon abrupt movement.

Until the instant invention, there remained a need for a nasal cannula suitable for use with infants which was resistant to compression and damage cause by pinching of the cannula and which could be used with supporting means attachable to the patient for preventing the cannula from being dislodged from the nasal passages while precluding the possibility of injury to the neonatal patient during the patient's movement in the neonatal environment.

SUMMARY OF THE INVENTION

The invention disclosed and claimed herein overcomes the aforementioned problems of the prior art in providing a nasal cannula and associated supporting means suitable for use with infants in a neonatal environment and presenting a substantially reduced possibility of compression interrupting air flow to and from the infant and pinching causing damage to the cannula, while precluding danger to the infant by obviating the need for a substantially rigid object connected between the patient and the cannula. More specifically, the present invention is directed to a nasal cannula having a body member made of a soft pliable material and including two hollow tubular prongs, each of which is terminated at a respective nasal end in a bulbus portion and has its opposite respirator end merging with a base having a bore in communication with the bores of the prongs, with the periphery of each of the prongs intermediate the nasal and respirator ends being ribbed to permit flexing of each prong without significant closure of the bore therein. A more rigid connector member has a nasal end adapted to be retained within the bore of the base of the nasal cannula and an axial bore in communication with the bores in the base and prongs of the cannula. The connector member has a respirator end adapted for removable engagement with a respirator hose. Means for stabilizing the cannula with respect to the neonatal patient are disclosed in the form of an elongated pliable and soft foam strip which the cannula body is adapted to securely receive and which can be fitted around the back of the neck of the patient. A skull cap made of a soft pliable foam material and having two or four foam strips extending therefrom for attachment to the base of the cannula is also disclosed. The foam strips are releasably received in the body of the cannula for securing the cannula prongs in the nostrils of the neonatal patient while the skull cap is worn on the head of the patient without danger of injury to the patient.

It is therefore an object of the invention to provide a nasal cannula suitable for use on an infant in a neonatal environment.

Another object of the invention is to provide a nasal cannula made of a very soft and pliable material which will not irritate the nasal passages of a neonate.

Still another object of the invention is to provide a nasal cannula having tubular prongs which can be partially bent without causing compression of the prongs to significantly block the tubular passages or damage the prongs.

A further object of the invention is to provide a nasal cannula of a soft pliable material which can be connected to a more rigid connector member for secure attachment to a respirator hose.

Still a further object of the invention is to provide a nasal cannula with a securing means suitable for securing the cannula in place when inserted into the nasal passages of an infant without presenting a potential danger to the infant.

Other and further objects of the invention will be apparent from the following drawings and description of a preferred embodiment of the invention in which like reference numerals are used to indicate like parts in the various views.

DESCRIPTION OF THE PREFERRED EMBODIMENTS

Figure 1:
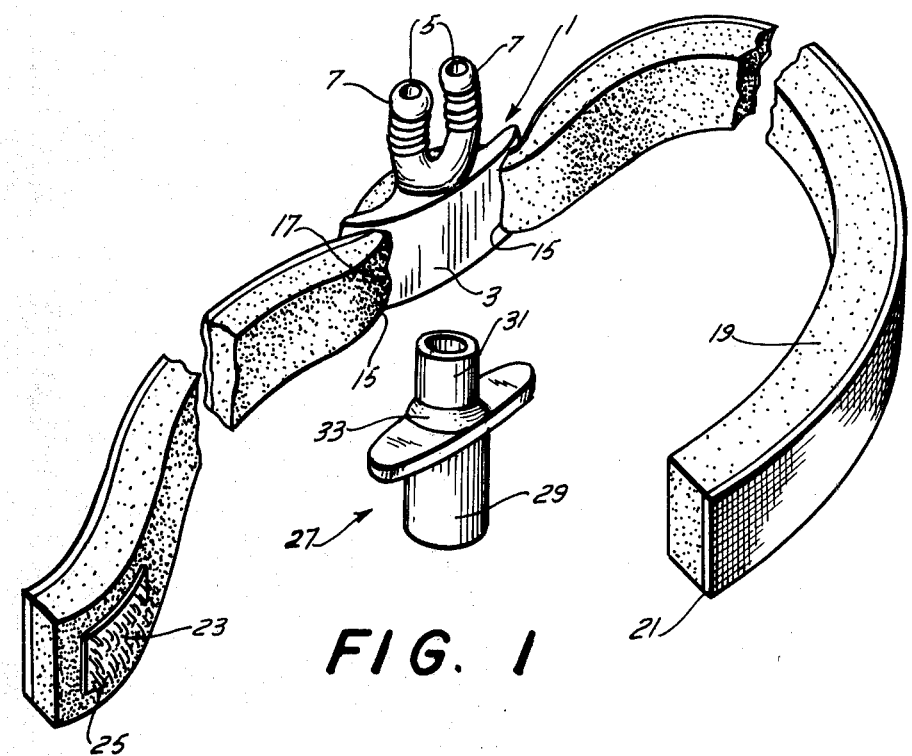
FIG. 1 is an exploded perspective view of a first embodiment of the apparatus of a preferred embodiment of the invention.
Figure 2:
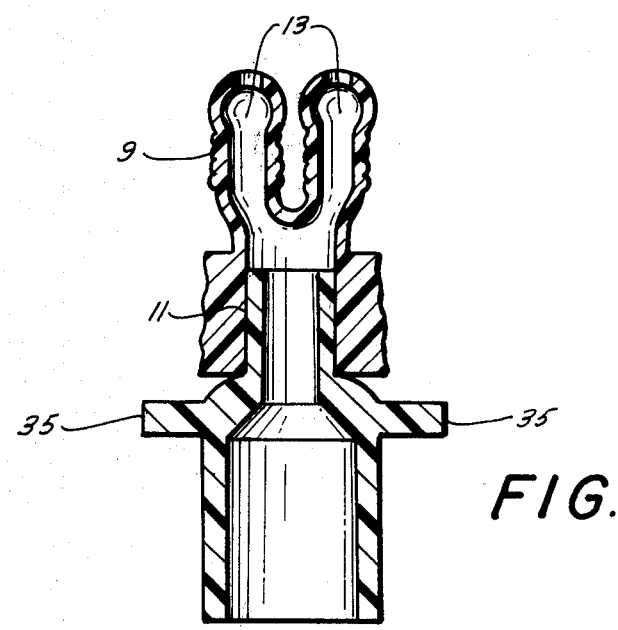
FIG. 2 is a sectional elevation view of a part of the apparatus of the preferred embodiment of the invention of FIG. 1.

Referring now to FIGS. 1 and 2 of the drawings, there is shown a nasal cannula 1 having a base 3 from which there upwardly extend two parallel spaced tubular prongs 5. The prongs 5 terminate at spaced nasal ends, adapted to be inserted into the nostrils of a neonatal patient, in bulbus portions 7 which are partially substantially spherically shaped. The prongs 7 converge at their respirator ends opposite the bulbus portions 7 where they merge together and into the base 3.

The hollow, tubular prongs 7 have respective bores 13 which communicate with an axial cylindrical bore 11 in the base 3 as can best be seen in FIG. 2.

The cannula 1 is molded from a very soft pliable rubber, plastic or similar material to prevent irritation to the nasal passages of the patient who may be a neonate, and to securely retain a securing means 19 which will subsequently be described.

The prongs 5 are provided on their outer circumferences with axially displaced circular ribs 9 integrally formed on the prong members 5 and occupying planes substantially normal to the respective longitudinal axes of the tubular prongs 5. The ribs 9 prevent significant compression and pinching of the prongs 5 which could block the tubular passages through the prongs 5 or overstress the soft rubber cannula material thereby causing damage to the cannula 1 upon bending or other movement of the prongs 5. A minimal amount of such movement is unavoidable during insertion of the prongs 5 of the cannula 1 into the nostrils of the patient. Moreover, since the patient for which the nasal cannula 1 is intended, will often be an infant who cannot appreciate the dangers of movement which would upset the cannula 1, such movement is likely to occur.

In the preferred embodiment of the invention, the axially displaced ribs 9 are substantially equally spaced from one another along the full lengths of the prongs 5 between the bulbus portions 7 and the region of merger of the prongs 5 with one another. Although the ribs are provided only on the exterior surface of the prongs 5 in the preferred embodiment of the invention, as this has been found sufficient to minimize pinching and compression, ribs may also be provided on the interior surfaces within the hollows of the tubular prongs 5 in symmetrical arrangement opposite the exterior ribs.

The base 3 of the nasal cannula 1 has outwardly extending wing portions in which there are formed apertures 15 having irregularities as at 17 to securely retain a soft strip 19 of foam-like or similar material which is inserted through the apertures as shown in FIG. 1 of the drawings. The foam strip 19 has one of its sides lined with a woven fiber material 21 which is also very soft and flexible. The material may be a natural soft material such as cotton or one of the woven synthetics, e.g., rayon or nylon. To one end of the foam strip 19 on the interior foam surface thereof, there is affixed a smaller plastic strip 23 having projections 25 adapted to be snagged within the woven fibers of the backing material 21. The foam strip 19 is of sufficient length to have both of its ends passed behind the neck of a neonatal patient after the prongs 5 of the cannula 1 are fully inserted into the nasal passages of the patient. The plastic strip 23 is then pressed against the fiber backing on the opposite end of the strip 19 to snag the projections 25 within the woven fibers of the backing 21 with the plastic strip 19 pulled reasonably taut so that the cannula 1 is secured on the neonate. Due to the softness and flexibility of both the foam strip 19, backing 21 and the nasal cannula 1, movement of the neonate tending to upset the cannula 1 or foam strip 19 will not cause any injury to the neonate.

The irregularities 17 in the apertures 15 are such as to cause the foam strip 19 to be compressed along its longitudinal central axis as it is forced through the apertures 15. The normal uncompressed cross section of the foam strip 19 is greater than the maximum width and height of the apertures 15 so that the foam strip must be compressed as it is passed through the apertures 15. Due to the resilience of the foam strip as it tends to expand after being compressed, the exterior surfaces of the foam strip 19 and backing 21 are urged against the irregular interior edges in the apertures 15 thereby increasing the friction between the foam strip 19 and the base 3 of the cannula 1 so that the foam strip 19 is securely held in place within the apertures 15 of the cannula 1.

Removably connected to the nasal cannula 1 is a connector 27 fabricated from a material more rigid than the soft rubber-like elastomeric material from which the cannula 1 is formed. The connector 27 has an enlarged cylindrical base 29 at its respirator end and a smaller diameter cylindrical hollow nipple 31 at its nasal end. The nipple 31 is seated on a rounded annular shoulder 33 which in turn is formed upon a flange having ears 35 extending diametrically outwardly from the nasal end of the cylindrical base 29. The exterior cylindrical periphery of the nipple 31 has a diameter slightly greater than that of the axial bore 11 in the base 3 of the nasal cannula 1 so that the nipple 31 can be inserted into and snuggly received in the axial bore in the base 3. Due to the elasticity of the rubber from which the cannula 1 is molded, the base 3 stretches to receive the nipple 31 thereby forming a resilient frictional coupling between the nasal cannula 1 and the connector 27.

The base 29 of the connector 27 is adapted to be attached to the end of a hose (not shown) leading from a respirator. Communication is provided from the enlarged cylindrical bore in the base 29 of the connector 27 to a narrower cylindrical bore in the nipple 31 portion of the connector 27 and through the bores 13 in the prongs 5 whereby air can be pumped between the respirator and the nasal passages of the patient in sealed protection from the external environment.

Figure 3:
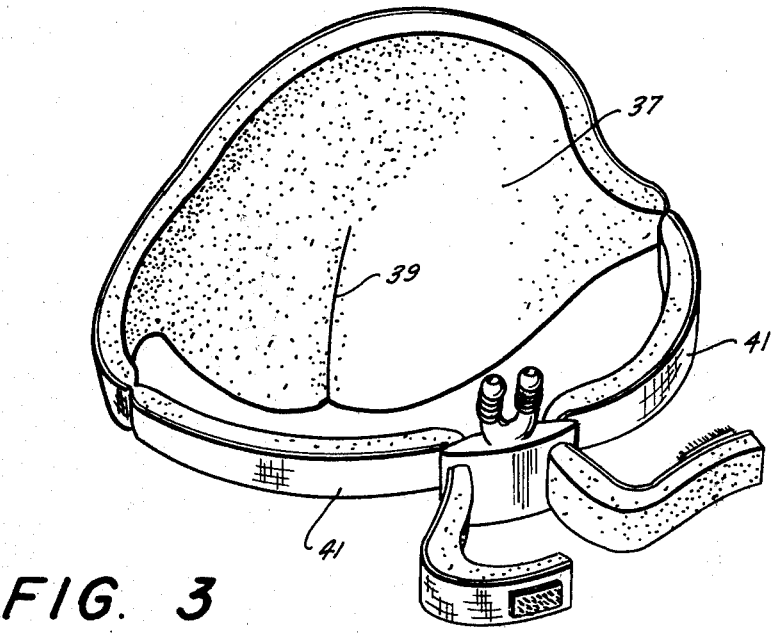
FIG. 3 is a perspective view of a second preferred embodiment of the invention, and, FIG. 4 is a perspective view of a third preferred embodiment of the invention.

Referring now the FIG. 3 of the drawings, there is shown a second preferred embodiment of the invention in which a nasal cannula similar to the one disclosed in connection with FIGS. 1 and 2 is attached to two foam strips similar to the ends of the one continuous foam strip 19 shown in FIG. 1. Two proximate ends of the foam strips 41 are equipped to be connected by means similar to the plastic strip 23 and fiber backing 21 of the strip shown in FIG. 1. However, unlike the embodiment of FIG. 1 where the plastic strip 23 is attached to the foam part of the strip, here the plastic strip is attached to the fiber backing so that each strip can be folded back upon itself. The opposite ends of the strips 41 are connected, by stitching, to a substantially circular piece of foam material covered by a fiber backing which material may but need not be the same as the material used for the foam strips 19 and their fiber backing 21. The irregular piece of foam material is formed into a skull cap 37 by slitting a radius of the material, removing a small sector thereof and sewing a seam in the material as at 39. The skull cap 37 may be placed upon the head of the neonate with the nasal cannula prongs 5 inserted in the nasal passages of the neonate. The end of the foam strip 41 having the projection bearing plastic connector member can then be pulled reasonably taut and snagged in the surface of the fiber material part of the strip 41.

Figure 4:
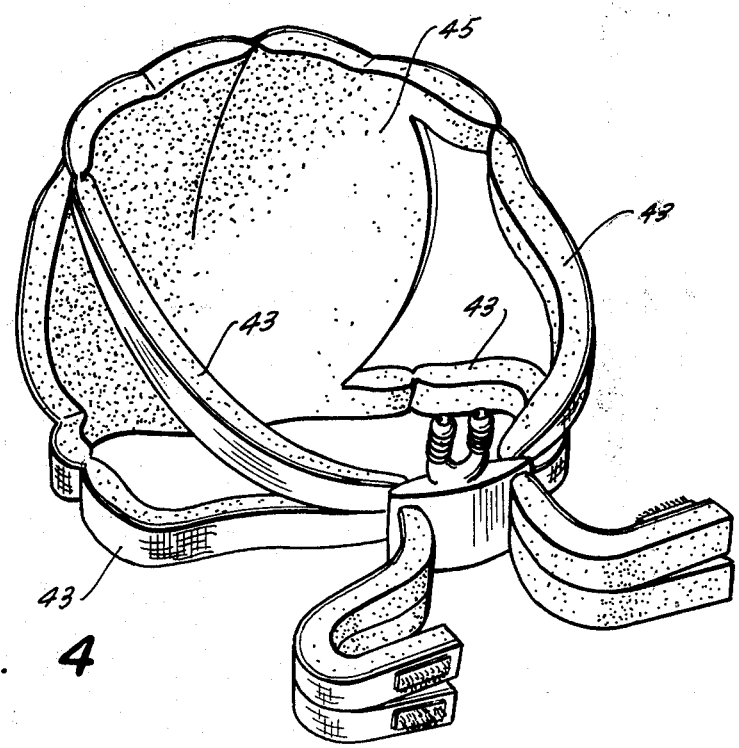

Referring to FIG. 4 of the drawings, there is shown a third preferred embodiment of the invention which differs from the embodiment of FIG. 3 in that four foam strips 43 of material with fiber backing are attached to four points, symetrically arranged and substantially equally angularly displaced from one another on a skull cap 45. Due to the compressable and resilient nature of the strips 43, two strips on either side of the skull cap can be passed through the apertures in the nasal cannula and securely held therein. The use of the four strips 43 provides a more stable securing of the cannula in the nostrils of the neonatal patient.

Instead of sewing the foam strips 41 and 43 to their associated skull caps, a skull cap with two or more integral foam strips extending from it can be cut from a flat piece of foam material with suitable fiber backing.

It is to be appreciated that the foregoing description is of several preferred embodiments of the invention to which many variations can be made without departing from the spirit and scope of the invention which is to be limited only by the following claims.

What is claimed is:

1. A nasal cannula for aiding the breathing of a patient by use of a respirator comprising:
a body made of a soft pliable material and including two hollow tubular bored prongs and a base, each prong having a nasal end and a respirator end, the respirator ends of the prongs merging adjacent said base, said base having an axial bore in communication with the bores of said prongs, the periphery of substantially the entire length of each prong intermediate said nasal and respirator ends being provided on its outer circumference with axially displaced circular ribs integrally formed and occupying planes substantially normal to the respective longitudinal axes of said tubular prong to permit flexing of each prong and substantially maintain the original cross-sectional diameter of the tubular bored prongs.

2. Apparatus according to claim 1 further comprising a bulbus portion integrally formed on the nasal end of each of said prongs.

3. Apparatus according to claim 2 wherein said prongs are ribbed along their entire lengths between the bulbus portions and the region of merger adjacent said base.

4. Apparatus according to claim 1 wherein said base has an aperture and further comprising means for tying said cannula to the patient securely receivable within said aperture.

5. Apparatus according to claim 4 wherein said tying means includes an elongated soft flexible strip.

6. Apparatus according to claim 4 further comprising a skull cap, and a plurality of flexible strips attached to said skull cap and secured to the base of the nasal cannula.

7. Apparatus according to claim 6 wherein said strips are attached to said skull cap at substantially equally angular displaced regions thereon.

8. Apparatus according to claim 1 further comprising a connector member having a nasal end, a respirator end and an axial bore extending from said nasal end to said respirator end, said connector member nasal end being snuggly received within the bore in the base of said body whereby the bores in said prongs are in communication with the bore in said connector member, said respirator end of said connector member being adapted for removable engagement with said respirator.

9. Apparatus according to claim 5 wherein said connector member is made from a material more rigid than the material from which said body is formed.

* * * * *

UNITED STATES PATENT AND TRADEMARK OFFICE
CERTIFICATE OF CORRECTION

PATENT NO. : 4,367,735

DATED : January 11, 1983

INVENTOR(S) : Carmelo Dali

It is certified that error appears in the above-identified patent and that said Letters Patent is hereby corrected as shown below:

Claim 9, line 1, "5" should read -- 8 --.

Signed and Sealed this

Tenth Day of May 1983

[SEAL]

Attest:

Attesting Officer

GERALD J. MOSSINGHOFF

Commissioner of Patents and Trademarks